United States Patent [19]

Lee

[11] Patent Number: 5,123,917
[45] Date of Patent: Jun. 23, 1992

[54] EXPANDABLE INTRALUMINAL VASCULAR GRAFT

[76] Inventor: Peter Y. Lee, 5118 Beechgrove NE., Canton, Ohio 44705

[21] Appl. No.: 516,104

[22] Filed: Apr. 27, 1990

[51] Int. Cl.$^5$ ............................................. A61F 2/06
[52] U.S. Cl. ........................................ 623/1; 623/11
[58] Field of Search ................................. 623/1, 12

[56] References Cited

U.S. PATENT DOCUMENTS

| | | | |
|---|---|---|---|
| 4,731,073 | 3/1988 | Robinson | 623/1 |
| 4,740,207 | 4/1988 | Kreamer | 623/1 |
| 4,776,337 | 10/1988 | Palmaz | 623/1 |

Primary Examiner—David Isabella
Assistant Examiner—Debra S. Brittingham
Attorney, Agent, or Firm—Fay, Sharpe, Beall, Fagan, Minnich & McKee

[57] ABSTRACT

An expandable intraluminal vascular graft includes a flexible cylindrical inner tube having a outer periphery and a plurality of separate scaffold member mounted on the outer periphery of the inner tube. The scaffold members are expandable, ring-like and provide circumferential rigidity to the graft. A flexible cylindrical outer tube concentrically encloses the inner tube and the plurality of scaffold members mounted thereon. The graft has a first diameter, which permits intraluminal delivery of the graft into a body passageway having a lumen, and a second expanded diameter, upon the application from the interior of the tube of a radially outwardly extending force. The second graft diameter is dependent on the amount of force applied so that he graft second diameter can be expanded to at least equal an internal diameter of the body passageway lumen. The scaffold members are deformed beyond their elastic limit when the graft is expanded to the second graft diameter.

18 Claims, 3 Drawing Sheets

EXPANDABLE INTRALUMINAL VASCULAR GRAFT

This invention relates to an expandable intraluminal vascular graft. More particularly, the present invention relates to a graft which is particularly useful for repairing blood vessels narrowed or occluded by disease.

Coronary angioplasty has now been performed for more than a decade. The initial success of the procedure is in the neighborhood of 80-85% with a restenosis rate in 6 months of approximately 30-40%. The advent of steerable guide wires and better balloon structures have increased the initial success rate to over 90%. Restenosis, however, remains at a fairly high level of approximately 30% in 6 months. Several attempts have been made to improve the long term success of this percutaneous procedure. They include the use of a coronary stent (of which there are several types), arthrectomy, and laser balloon angioplasty. The recurrence rate, however, is not significantly improved from that of angioplasty.

The atheromatous plaques that are subjected to angioplasty are a heterogeneous group pathoanatomically. After angioplasty, there is fissuring of the atheromatous plaque and exposure of the media and cholesterol filled atheromatous cavity to the fluid in the blood stream. These tissues are thrombogenic and may set up an acute closure because of thrombosis. Other locally produced enzymes such as "platelet derived growth factors" promote healing with such an exuberant growth that the vascular lumen is reoccluded subsequently. One potential way to combat such an exuberant tissue growth is to recreate a suitable surface whereby healing could occur in a more controlled fashion. This surface should be non-thrombogenic and should allow an orderly endothelization to occur. It should also act as a physical barrier so that the hematological elements do not come in contact with injured intimal and medial vessel walls thereby eliminating the interaction between the hematological elements and the exposed thrombogenic tissue. Furthermore, a physical barrier would ensure that the growth and proliferation of the vascular media does not encroach upon the vascular lumen.

It is desirable in various situations to provide a means for expanding a constricted vessel or for maintaining an open passageway through a vessel. Such situations arise, for instance, after angioplasty of a blood vessel. In these situations, wire stents have proven useful to prevent restenosis of the dilated vessel or to eliminate the danger of occlusion caused by "flaps" resulting from intimal tears associated with angioplasty. Wire stents can also be used to reinforce structures on the point of collapse in the respiratory or the brachial tracts.

Structures which have previously been used as intraluminal vascular grafts have included coiled stainless steel springs; helically wound coil springs manufactured from an expandable heat sensitive material; and expandable stainless steel stents formed from stainless steel wire configured into a zig zag pattern. Inasmuch as all of these structures must be delivered to the desired location within a given blood vessel or other body passageway in a collapsed state, in order to pass through the passageway, there is no effective control over the final expanded configuration of these structures. If the diameter of the desired body passageway has been miscalculated, an undersized graft might not expand enough to contact the interior surface of the passageway so as to be secured thereto. It may then migrate away from the desired location. Likewise, an oversized graft might expand to such an extent as to cause a rupturing of the body passageway. Moreover, the constant outwardly radiating pressure exerted on the interior surface of the body passageway can cause erosion of the internal surface, or intima, of the body passageway.

Another type of stent device is comprised of a thin walled tubular member having a plurality of slots formed therein so as to enable the tubular member to be deformed from an initial smaller diameter, which permits delivery into the body passageway, to a final radially expanded diameter so as to be secured in the body passageway. However, this device also has several drawbacks, such as inadequate longitudinal flexibility to enable the stent to be delivered into a serpentine body passage, such as a blood vessel, and its failure to provide a physical barrier between the walls of the blood vessel and the blood flowing therethrough. In the absence of such a barrier the slots formed in the tubular member act as a locus for the migration of mesothelial cells which then grow on the graft and into the vascular passage.

Accordingly, it has been considered desirable to develop a new and improved intraluminal vascular graft which would overcome the foregoing difficulties and others while providing better and more advantageous overall results.

BRIEF SUMMARY OF THE INVENTION

In accordance with the present invention, a new and improved expandable intraluminal vascular graft is provided.

More particularly in accordance with this aspect of the invention, the graft comprises a flexible cylindrical inner tube having an outer periphery and a plurality of separate expandable ring-like scaffold members which are secured to the inner tube outer periphery in spaced relation to each other. The scaffold members provide circumferential rigidity to the graft. A flexible cylindrical outer tube concentrically encloses the inner tube and the plurality of scaffold members secured thereto. The graft has a first diameter which permits intraluminal delivery of the graft into a body passageway having a lumen. The graft also has a second expanded diameter upon the application from the interior of the inner tube of a radially outwardly extending force. The second graft diameter is dependent upon the amount of force applied so that the graft second diameter can be expanded to at least equal an internal diameter of the body passageway lumen. The scaffold members are deformed beyond their elastic limit when the graft is expanded to the second graft diameter.

According to another aspect of the invention, an expandable intraluminal vascular graft is provided.

More particularly in accordance with this aspect of the invention, the graft comprises a flexible cylindrical conduit having first and second ends, a luminal inner separate stiffening rings are each secured to one of the conduit inner and outer surfaces. The stiffening rings provide circumferential stiffness to the conduit. The stiffening rings are spaced from each other to allow the graft to be flexible along its longitudinal axis.

According to still another aspect of the invention, a prosthetic blood conduit is provided for a body.

More particularly in accordance with this aspect of the invention, the conduit comprises a flexible cylindrical inner tube having first and second ends, a luminal inner surface and an outer surface. A flexible cylindrical outer tube encircles the inner tube and has an inner surface and a vascular outer surface. The outer tube first and second ends overlie the first and second ends of the inner tube. A plurality of separate stiffening rings, each encircling the inner tube, are secured between the inner tube outer surface and the outer tube inner surface. The stiffening rings, which are spaced away from each other, provide circumferential stiffness to the conduit.

According to yet another aspect of the invention, an endothelial liner for a vein or an artery of a body is provided.

More particularly in accordance with this embodiment of the invention, the liner comprises an inner membrane comprising a cylindrical tube of pliable material having a luminal side with minimal thrombogenic potential and an outer membrane enclosing the inner membrane. The outer membrane comprises a cylindrical tube of pliable material having a vascular side with minimal tissue reaction potential. A plurality of stiffening elements are disposed between the inner and outer tubes to provide the liner with circumferential stiffness. The elements are spaced from each to allow the liner to be flexible along its longitudinal axis.

In accordance with still yet another aspect of the invention, a method is provided for implanting an expandable intraluminal vascular graft.

More particularly in accordance with this aspect of the invention, the method comprises providing a thin walled tubular graft including an inner tube, an outer tube enclosing the inner tube and a plurality of spaced stiffening rings secured between the inner and outer tubes. The graft is disposed on a catheter and the graft and catheter are thereupon inserted into an artery or vein. The graft is expanded at a desired location within the artery or vein from a first smaller diameter to a second larger diameter by expanding a portion of the catheter disposed within the graft to force the graft radially outwardly into contact with the vein or artery. The stiffening rings of the graft are deformed beyond their elastic limit to permanently maintain the graft at the second larger diameter.

One advantage of the present invention is the provision of a new and improved expandable intraluminal graft.

Another advantage of the present invention is the provision of a graft having a plurality of spaced stiffening elements to allow the graft to have circumferential rigidity and at the same time have longitudinal flexibility.

Still another advantage of the present invention is the provision of a graft having a luminal side made from a material having a minimal thrombogenic potential.

Yet another advantage of the present invention is the provision of a graft having a vascular side made of a material which does not promote intimal tissue proliferation.

A further advantage of the present invention is the provision of a graft which includes a cylindrical inner layer that is enclosed by a cylindrical outer layer such that secured between the inner and outer layers are a plurality of spaced expandable ring-like scaffold elements.

A still further advantage of the present invention is the provision of a graft which serves as physical barrier inbetween a vascular passageway and the blood flowing therethrough. The separation of blood elements from the blood vessel wall prevents the blood-borne hormones from stimulating the vessel wall into an abnormal growth pattern.

A yet further advantage of the present invention is the provision of a graft which does not change in length as it is expanded from its initial diameter to its final diameter.

Still other benefits and advantages of the invention will become apparent to those skilled in the art upon a reading and understanding of the following detailed specification.

BRIEF DESCRIPTION OF THE DRAWINGS

The invention may take physical form in certain parts and arrangements of parts preferred and alternate embodiments of which will be described in detail in this specification and illustrated in the accompanying drawings which form a part hereof and wherein.

DETAILED DESCRIPTION OF THE PREFERRED AND ALTERNATE EMBODIMENTS

Figure 1:
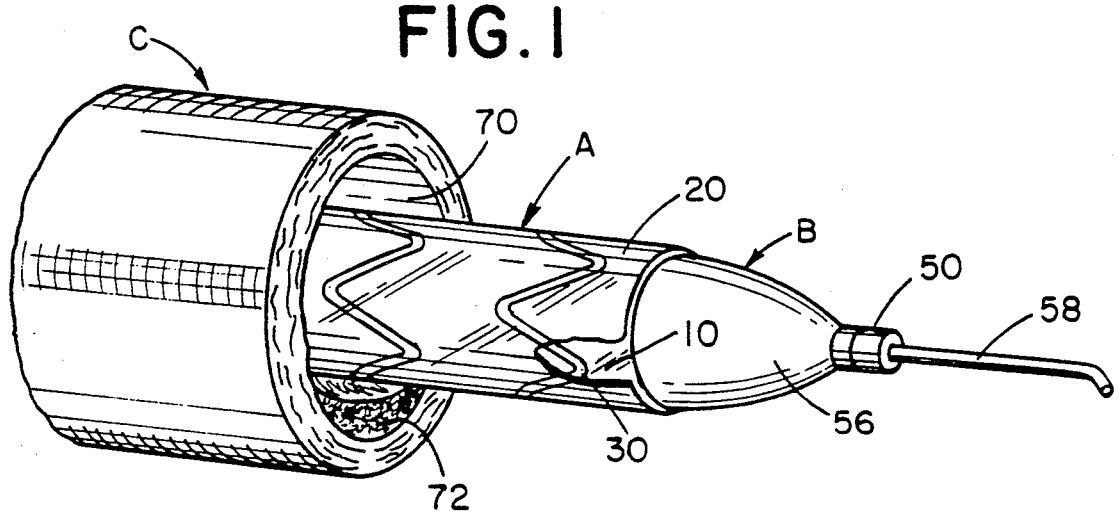
FIG. 1 is a perspective view illustrating a portion of a body artery or vein with the graft according to the present invention extending therethrough as carried by a catheter.

Referring now to the drawings wherein the showings are for purposes of illustrating preferred and alternate embodiments of the invention only and not for purposes of limiting same, FIG. 1 shows the preferred embodiment of the subject new graft A as it is mounted on a catheter B and moved longitudinally in a vascular passage C.

Figure 4:
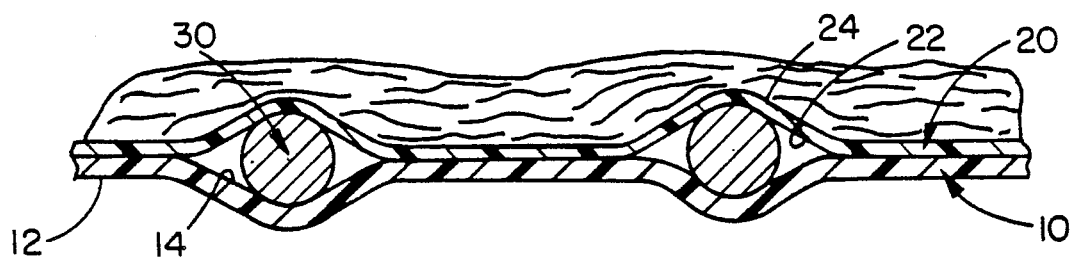
FIG. 4 is a greatly enlarged cross-sectional view of a portion of FIG. 3.

With reference now more particularly to FIG. 4, the graft includes an inner layer 10 having an inner surface or luminal surface 12 and an outer surface 14. The inner layer or membrane can be made from PTFE (polytetrafluoroethylene) or another suitable material such as porous polyurethane. PTFE has been used fairly extensively as a vascular prosthesis and has known properties. It also has the best patency statistics in small artery replacements down to around 4 mm. If necessary, the luminal surface 12 could also be coated with various pharmacological agents, such as Prostaglandin $E_1$ or $I_2$, cAMP (i.e., cyclic AMP) or heparin to impede platelet adhesion. Subsequent monocytic/fibroblastic proliferation could be impeded with, for example, Prostaglandin $E_1$ or $I_2$ corticosteroids, cytotoxic antitumor agents or heparin.

An outer layer 20 encloses the inner layer and includes an inner surface 22 as well as an outer or vascular surface 24 which preferably has minimal tissue reaction potential. The outer layer or membrane 20 could also be made of a PTFE material since it is presumed this material's interaction with vascular media is probably just as good as is its reaction with blood. However, other potential materials for this application also include dacron or a proline mesh or the like. The material should be rather inert and should not promote a significant amount of scar formation. Also, if desired, drug impregnation in the outer layer vascular surface, such as with corticosteroids or cytotoxic antitumor agents, may minimize tissue proliferation.

Figure 3:
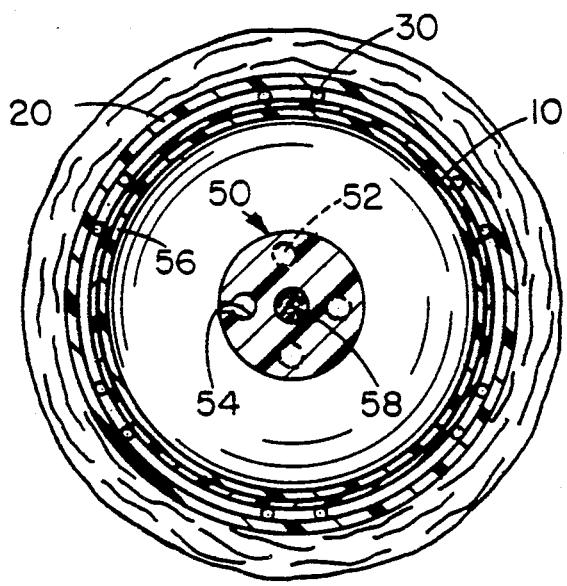
FIG. 3 is a cross-sectional view through the body lumen graft and catheter of FIG. 2 along line 3-3.

As illustrated in FIGS. 1 and 3, the inner and outer layers 10 and 30 preferably are cylindrical in shape and are so positioned with respect to each other that the ends of the outer layer overlie the ends of the inner layer.

Figure 5:
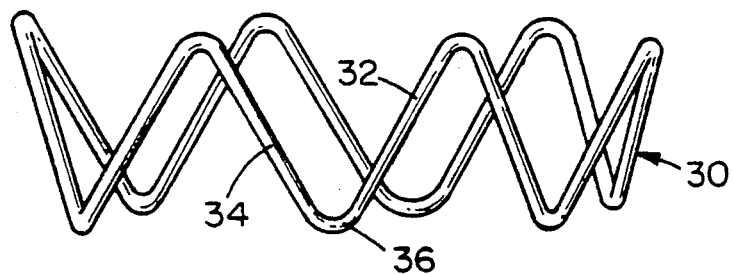
FIG. 5 is a side elevational view of a single scaffold member of the type utilized in the graft of FIGS. 1-4.

Positioned between the inner layer 10 and the outer layer 20 are a plurality of spaced scaffold members 30. With reference now more particularly to FIG. 5, it can be seen that each scaffold member 30 is ring-like and includes a plurality of angled straight sections 32 and 34 which are connected at bends 36.

Figure 2:
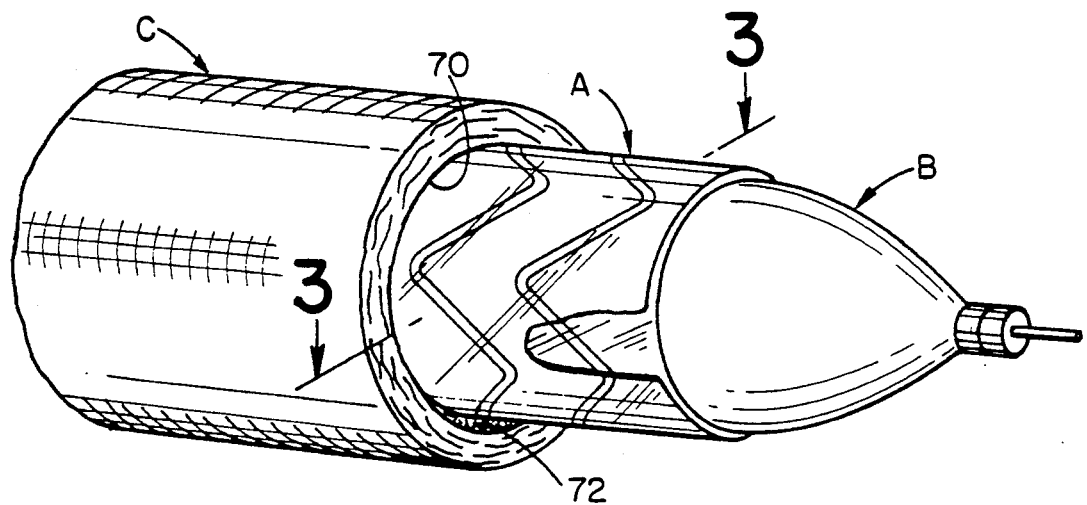
FIG. 2 is a perspective view of the body lumen graft and catheter after the graft has been expanded.

The scaffold should be constructed of materials that have minimal tissue reaction and do not provoke a significant injury response. One suitable material can be a surgical stainless steel. The rings 30 can be secured to the inner liner 10 by a suitable means such as an adhesive layer. Alternately, the rings can be secured between the inner and outer liners 10, 20 during the manufacturing process, such that the liner layers are adhered to each other between the scaffolds thereby trapping the scaffolds in pockets formed between the liner layers. The spacing of the rings 30 from one another is dependent on how much radial stiffening it is desired to provide the graft. As mentioned, radial stiffening is necessary in order to expand a constricted vessel and in order to maintain an open passageway through a vessel. The spacing of the rings from one another is also dependent on how the ring changes its configuration as the graft or conduit is expanded from its contracted position, as illustrated in FIG. 1, to its expanded position, as illustrated in FIG. 2. The rings 30 can be spaced apart by between 3 and 4 mm if desired, but this is somewhat dependent on the material used for the rings.

The spacing of the rings 30 from each other allows for the maximum amount of maneuverability of the graft along its longitudinal axis while maintaining the radial stiffness of the graft. The spacing of the rings therefore allows for maximal longitudinal flexibility in order to allow the graft to enter tortuous lumens in the body, such as various vascular passages. The graft is sufficiently pliable so that it can be folded during insertion into a vascular lumen and is sufficiently thin, in its unexpanded state, so that it does not impinge upon the vascular lumen when the graft is unfolded adjacent an atheromatous plaque.

The inner layer 10 can have a thickness of approximately 50 micrometers or less while the outer liner 20 can have a thickness of approximately 50 to 100 micrometers. Preferably the scaffold member 30 has a circular cross-section with a diameter of approximately 0.1 to 0.2 mm.

The graft A is so designed that it can be mounted on a standard commercially available balloon catheter B, and, once mounted, the graft is moved along the lumen or passage C to the appropriate location therein. As shown in FIG. 3, the catheter includes a body 50 having one or more lumens 52, 54 extending therethrough as well as a balloon 56 positioned adjacent a distal end of the body 50. One of the lumens 54 of the body terminates within a space enclosed by the balloon 56 in order to allow the balloon to be inflated when desired. Preferably, the catheter is of the type having a central lumen 57 which can accommodate a stiffening wire 58.

As illustrated in FIG. 1, the lumen C is a vascular passageway which includes an inner wall 70 on which is formed an atheromatous plaque 72. The intent of the graft A is to compress this plaque 72 by the expansion of the graft A thereby allowing a greater passage diameter for blood flow. This is illustrated in FIG. 2 where the catheter balloon 56 is expanded thereby also radially expanding outwardly the graft A. More specifically, the inner and outer layers 10, 20 stretch radially outwardly and the scaffold member 30 is deformed beyond its elastic limit as it is radially enlarged. During this deformation, the angle between the several adjacent straight sections 32, 34 of the scaffold member 30 changes. More specifically, the included angle between the straight sections becomes larger as the radius of the scaffold member 30 increases.

The end result of the inflation of the graft A is that the plaque 72 is compressed as is illustrated in FIG. 2 and a larger cross-sectional flow area is provided through the blood passage C.

However, the graft A will prevent the exuberant growth of tissue at lesions formed by the conventional balloon angioplasty since a suitable vascular surface is created where healing can occur in a more controlled fashion. The luminal surface is non-thrombogenic and allows an orderly endothelialization to occur. The graft A also acts as a physical barrier so that hematological elements, i.e., various blood particles, do not come into contact with the injured intimal and medial vessel walls. This eliminates the interaction between the blood components and exposed thrombogenic tissue. Moreover, the graft acts as a barrier so that growth and proliferation of vascular media does not encroach upon the vascular lumen.

With the graft A of the present invention, the injured blood vessel C faces the resurface liner on the vascular side rather than in an end to end anastomotic fashion as in the prior art. Therefore, growth of the endothelium and realigning of the liner on the luminal side will be considerably different because the resurface device will come in contact at its ends with areas of the vessel C that have an intact vascular endothelium.

The membranous layers or liners 10 and 20 are mounted on the scaffold members 30 so that the scaffold members will serve both to anchor the graft A to the vascular wall and to withstand the pressure of cellular growth that would normally tend to distort the cross-sectional size of the graft.

If the device can be made to have a survival rate approaching that of saphenous vein bypass graft surgery, then the graft would be a superior alternative to that of venous revascularization because this procedure does not require a surgery.

While the procedure is designed with the coronary artery in mind, it can certainly be applied to the peripheral vascular tree as well. In fact, the survival of this type of device in large vessels may indicate that the use of this device in the peripheral vascular tree is particularly advantageous.

Figure 6:
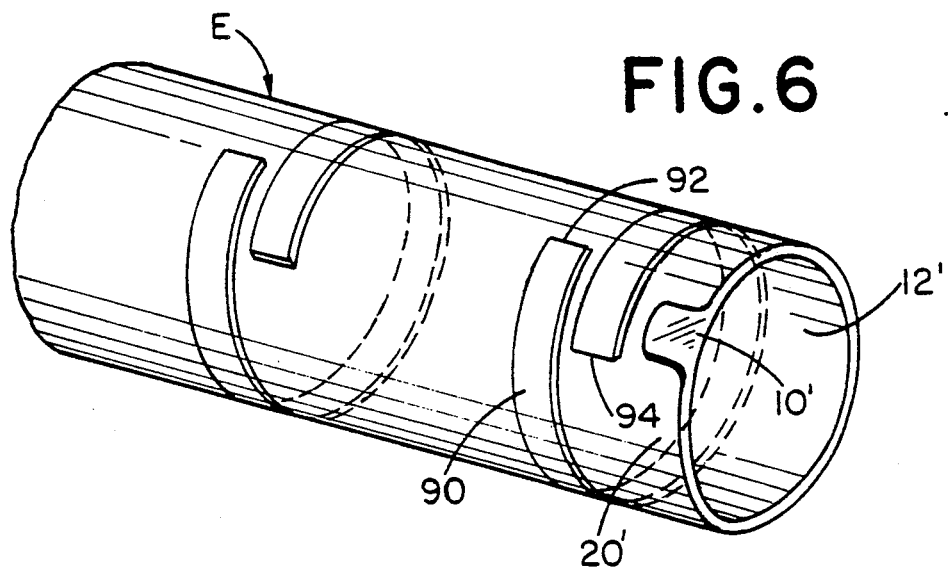
FIG. 6 is a perspective view of a graft according to an alternate embodiment of the present invention in its contracted form.
Figure 7:
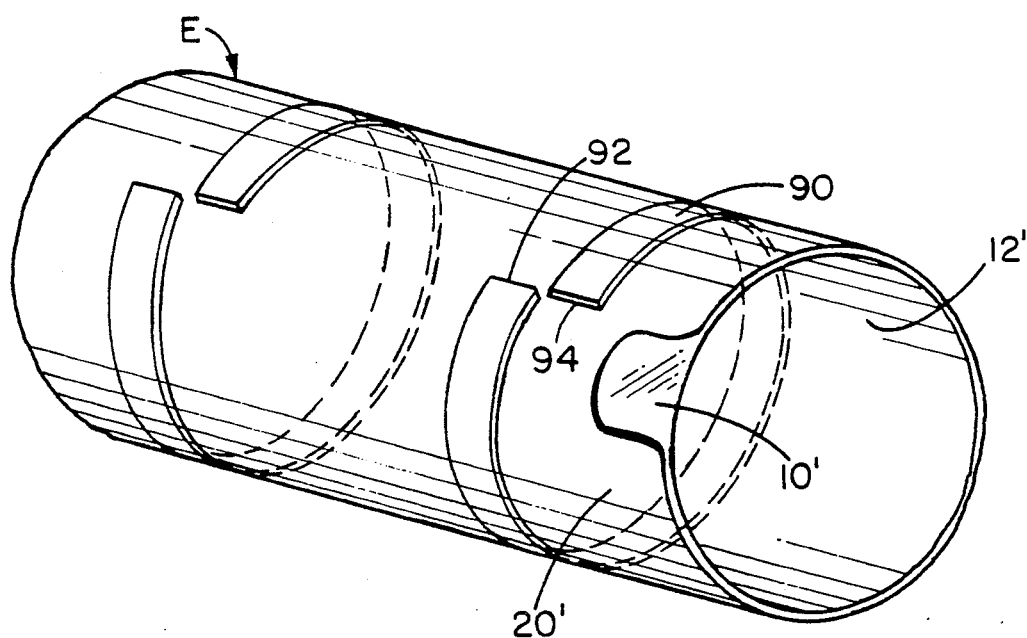
FIG. 7 is a perspective view of the graft of FIG. 6 in its expanded form.

With reference now to FIGS. 6 and 7, an alternate embodiment of the present invention is there illustrated. For ease of understanding this alternative, like components are identified by like numerals with a primed (')

suffix and new components are identified by new numerals.

As shown in FIG. 6, the graft E includes an inner layer 10' and an outer layer 20'. Disposed between the two layers is a ring member 90 having first and second ends 92, 94 that are spaced from each other both longitudinally and circumferentially. In its unexpanded state, as illustrated in FIG. 6, the ring ends 92, 94 overlap each other. However, when the graft E is expanded as shown in FIG. 7, the ring ends 92, 94 preferably approach each other so that they lie along a common longitudinally extending line. However, the ends are still circumferentially spaced from each other as is illustrated. The ring is deformed beyond its elastic limit when the graft E is expanded, and this insures that the graft will not collapse again after expansion. As in the first embodiment, a suitable balloon catheter can be brought up against an inner surface 12' of the inner layer in order to expand the graft to its final radial dimensions as shown in FIG. 7.

While the preferred embodiment of the graft A is shown as having separate inner and outer layers 10 and 20, it should be appreciated that conceptually the two layers could instead be just the inner and outer surfaces of the same membrane. In that case, the spaced scaffold members 30 could be secured either to the exterior or the interior surface of the membrane as found desirable for a particular use.

Figure 8:
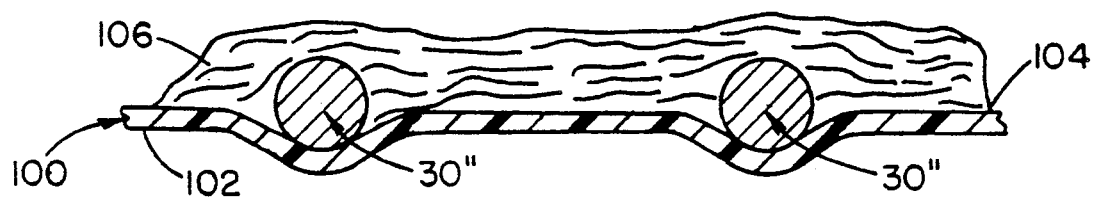
FIG. 8 is a greatly enlarged cross-sectional view of a graft according to a second alternate embodiment of the present invention.

With reference now to a second preferred embodiment of the present invention as illustrated in FIG. 8, the invention is there shown as being utilized in a single membrane-type of conduit. For ease of illustration and appreciation of this alternative, like components are identified by like numerals with a double primed (") suffix and new components are identified by new numerals.

In FIG. 8, a flexible, cylindrical conduit 100 is illustrated which has an inner or luminal surface 102 and an outer or vascular surface 104 that joins a blood vessel inner periphery 106. A plurality of separate stiffening rings 30" are provided which are secured to one of the conduit inner surface and outer surface.

It would be advantageous to put the rings or scaffold members 30 on the inside surface in order to hold the membrane out against the vascular surface and not let it contract in diameter. On the other hand, it would be advantageous to provide the rings on the outside in order not to have any barrier to blood flow through the graft. Most likely, the rings would be secured to the outside surface of the graft.

The rings 30" are therefore shown as being secured to the outside surface of the graft or conduit 100. It is noted that the stiffening rings 30" are spaced from each other to allow the graft to be flexible along its longitudinal axis while at the same time enabling the graft to be stiff in a radial direction so as to prevent a narrowing of the flow diameter through the vascular lumen in which the graft sits.

The invention has been described with reference to preferred and alternate embodiments. Obviously, modifications and alterations will occur to others upon the reading and understanding of this specification. It is intended to include all such modifications and alterations insofar as they come within the scope of the appended claims or the equivalents thereof.

What is claimed is:

1. An expandable intraluminal vascular graft, comprising:

a longitudinally flexible and radially expandable cylindrical inner tube having an outer periphery and an interior surface;

a plurality of separate, expandable, ring scaffold members which are mounted on said outer periphery along a length of said inner tube in spaced relation to each other, said scaffold members providing circumferential rigidity to the graft; and, a longitudinally flexible cylindrical and raidally expandable outer tube concentrically enclosing said inner tube and said plurality of scaffold members mounted thereon, wherein the graft has a first diameter which permits intraluminal delivery of the graft into a body passageway having a lumen, and wherein the graft has a second, expanded diameter, upon the application from the interior surface of said inner tube of a radially outwardly extending force, said second graft diameter being dependent on the amount of the extending force applied so that said graft second diameter can be expanded to at least equal an internal diameter of said body passageway lumen, wherein said scaffold members are deformed beyond their elastic limit when the graft is expanded to said second graft diameter.

2. The graft of claim 1 wherein each of said plurality of scaffold members comprises an elongated element which is formed in an endless loop and has a plurality of straight sections that are angled in relation to each other.

3. The graft of claim 2 wherein said plurality of angled sections have a first, smaller included angle in relation to each other when said graft is at its first diameter and a second, larger included angle when said graft is at its second, expanded diameter.

4. The graft of claim 1 wherein each of said plurality of scaffold members comprises an elongated body having opposed ends which are positioned in spaced planes extending normal to a longitudinal axis of the graft.

5. The graft of claim 4 wherein said elongated body comprises a band having opposed ends which overlap each other when the graft is at said first graft diameter.

6. The graft of claim 1 wherein said plurality of scaffold members is secured between said inner tube and said outer tube by an adhesive.

7. The graft of claim 1 wherein said inner tube is continuous along its length so as to form a solid barrier against the body passageway.

8. An expandable intraluminal vascular graft comprising:

a longitudinally flexible and radially expandable cylindrical conduit having a predetermined length terminating at first and second ends, a luminal inner surface and a vascular outer surface; and, a plurality of separate stiffening rings each being secured to one of said conduit inner surface and outer surface, said stiffening rings being spaced from each other along the length of said conduit from said first end to said second end providing circumferential stiffness to said conduit, said stiffening rings being spaced from each other to allow the graft to be flexible along its longitudinal axis wherein the graft has a first diameter which permits intraluminal delivery of the graft into a body passageway having a lumen, and wherein the graft has a second, expanded diameter, upon the application from the interior of said conduit of a radially outwardly extending force, said second graft diameter being dependent on the amount of force applied so that said graft second diameter can be expanded to at least equal an internal diameter of said body passageway lumen, wherein said stiffening rings are deformed beyond their elastic limit when the graft is expanded to said second graft diameter.

9. The graft of claim 8 wherein said conduit comprises:
an inner tube having first and second ends; and,
an outer tube, having first and second ends, which encircles said inner tube such that said first and second ends of said outer tube overlie said first and second ends of said inner tube.

10. The graft of claim 8 wherein said conduit is continuous along its length to form a solid barrier against the body passageway.

11. A prosthetic blood conduit for a body comprising:
a flexible cylindrical inner tube having a predetermined length terminating at first and second ends, a luminal inner surface and an outer surface;
a flexible cylindrical outer tube encircling said inner tube and being secured thereto, said outer tube having an inner surface and a vascular outer surface, said outer tube having first and second ends, which overlie said first and second ends of said inner tube; and,
a plurality of separate stiffening rings each encircling said inner tube and secured between said inner tube outer surface and said outer tube inner surface, said stiffening rings being spaced from each other along the length of said conduit from said first end to said second end providing circumferential stiffness to the conduit and being spaced from each other wherein said inner tube, stiffening rings and outer tube are expandable from a respective first diameter at which the conduit is transported through a lumen of the body to a respective second enlarged diameter at which the conduit is secured in place in the lumen of the body and wherein the expansion of the conduit from the respective first diameters to the respective second diameters is accomplished by a balloon, located on an associated catheter, that is positioned within the conduit.

12. The conduit of claim 10 wherein said stiffening rings each comprise an elongated element having a plurality of straight sections which are angled with respect to each other.

13. The conduit of claim 10 wherein said stiffening rings each comprise an elongated band having ends which are located adjacent each other such that the ends are positioned in separate adjacent planes expending normal to a longitudinal axis of the graft.

14. The conduit of claim 10 further comprising a pharmacological agent coating said inner tube luminal side to impede platelet adhesion.

15. The conduit of claim 10 further comprising a pharmacological agent coating said inner tube luminal side to impede monocytic/fibroblastic proliferation.

16. The conduit of claim 10 further comprising a pharmacological agent coating said outer tube vascular side to impede ultimal proliferation.

17. An endothelial liner for a vein or an artery of a body, comprising:
an inner membrane comprising a cylindrical tube of a pliable continuous radially expandable material having a luminal side with minimal thrombogenic potential;
an outer membrane enclosing said inner membrane, said outer membrane comprising a cylindrical tube of a pliable continuous radially expandable material having a vascular side with minimal tissue reaction potential; and,
a plurality of stiffening elements disposed between said inner and outer tubes to provide the liner with circumferential stiffness, said elements being spaced from each other disposed along a length to allow the liner to be flexible along its longitudinal axis wherein said inner and outer membranes and said stiffening elements are expandable from a first respective diameter, at which they are introduced into a vein or artery of the body, to a second respective diameter at which they are operatively secured in the vein or artery of the body.

18. The liner of claim 17 wherein said stiffening elements each comprise a ring-shaped member which is so formed that it can be expanded from a first smaller diameter to a second larger diameter, said member being formed from a material which during expansion exceeds its elastic limit so that it is permanently deformed to said second larger diameter.

* * * * *